(12) United States Patent
Mudry et al.

(10) Patent No.: US 10,539,494 B1
(45) Date of Patent: Jan. 21, 2020

(54) PORTABLE APPARATUS FOR TESTING OR CALIBRATION OF A PARTICULATE EMISSION MONITOR

(71) Applicant: AIRFLOW SCIENCES EQUIPMENT LLC, Livonia, MI (US)

(72) Inventors: Robert G. Mudry, Plymouth, MI (US); Bruce R. Devlin, Brighton, MI (US); Jeffrey D. Everett, Livonia, MI (US)

(73) Assignee: AIRFLOW SCIENCES CORPORATION, Livonia, MI (US)

( * ) Notice: Subject to any disclaimer, the term of this patent is extended or adjusted under 35 U.S.C. 154(b) by 447 days.

(21) Appl. No.: 15/581,076

(22) Filed: Apr. 28, 2017

Related U.S. Application Data

(60) Provisional application No. 62/330,790, filed on May 2, 2016.

(51) Int. Cl.
*G01N 15/10* (2006.01)
*G01N 15/06* (2006.01)

(52) U.S. Cl.
CPC ......... *G01N 15/1012* (2013.01); *G01N 15/06* (2013.01)

(58) Field of Classification Search
CPC .......... G01P 21/00; G01D 3/022; G01D 3/08; G01D 18/00; G01N 33/0006; G01N 27/4163; G01N 15/1012; G01N 2015/1025; G01N 2203/0246; G01N 27/4715; G01N 30/8665; G01N 33/007; G01N 2223/303; G01N 29/30; G01N 17/004; G01N 17/00; G01N 17/002; G01F 25/0053; G01F 1/36; G01F 25/003; G01L 27/00; A61B 5/02156; A61B 5/02141; F16K 37/0075; A23L 3/22; G01M 17/0074; G01M 17/007; G01M 17/0072
USPC ...... 73/1.06, 865.6, 1.26, 1.67, 1.69, 118.01, 73/1.01, 1.02
See application file for complete search history.

(56) References Cited

U.S. PATENT DOCUMENTS

| | | | | |
|---|---|---|---|---|
| 5,150,036 A | * | 9/1992 | Pourprix | G01N 15/0656 324/601 |
| 5,502,998 A | * | 4/1996 | Miller | G01N 1/2273 73/1.06 |
| 5,824,918 A | * | 10/1998 | Zuk | G01N 17/002 73/865.6 |
| 7,229,593 B1 | * | 6/2007 | Ho | G01N 13/00 422/50 |
| 7,621,192 B2 | * | 11/2009 | Conti | G01N 3/56 623/912 |
| 8,372,187 B2 | * | 2/2013 | Gidney | C09C 1/48 73/28.01 |
| 8,573,034 B2 | * | 11/2013 | Grant | G01N 1/4077 73/1.02 |
| 2014/0077100 A1 | * | 3/2014 | Hasegawa | G01N 15/1012 250/459.1 |
| 2017/0082573 A1 | * | 3/2017 | Vingerhoets | G01N 27/416 |

* cited by examiner

*Primary Examiner* — John Fitzgerald
*Assistant Examiner* — Truong D Phan
(74) *Attorney, Agent, or Firm* — George L. Boller

(57) ABSTRACT

A particulate matter emission monitor for monitoring concentration of particulate matter concentration in a fluent stream passing through an industrial stack is tested and/or calibrated using apparatus which is scaled down in size from the much larger industrial stack.

20 Claims, 3 Drawing Sheets

PORTABLE APPARATUS FOR TESTING OR CALIBRATION OF A PARTICULATE EMISSION MONITOR

FIELD OF THE INVENTION

This invention relates to a portable apparatus for testing and/or calibration of a particulate matter emission monitor which monitors particulate matter concentration in a fluent stream.

BACKGROUND OF THE INVENTION

Many industrial processes require, either by way of self-imposed constraints or government regulations, that the concentration of certain particulate matter (PM) suspended in a particular fluid (e.g., a gas) not exceed a specified PM concentration threshold. Compliance of a process with a specified PM concentration threshold can be ascertained either periodically or continuously by a PM emission monitor which comprises an array of sensors. If the PM of interest is entrained in a fluent stream that is discharged into the environment, government regulations may require that PM concentration be continuously monitored using sensors that are part of a Continuous Emissions Monitoring System (CEMS).

Integration of a PM emission monitor into a particular CEMS at an industrial facility stack may require periodic calibration of the PM emission monitor in order to maintain accurate readings over time. The necessity and frequency of the calibrations may be prescribed by government regulations, by the manufacturer, or by the end user. In some industrial operations it may be difficult to perform such calibrations, which inherently require that the quantity of PM being discharged from the duct or stack be varied over a range of flow rates. Purposely increasing the PM emissions, for instance, in order to calibrate an installed PM monitor, may result in disruptions to operating equipment and negatively affect the production process at the facility. Facilities would prefer to perform calibration without interrupting the industrial operation which is being monitored.

SUMMARY OF THE INVENTION

The present invention provides a solution for calibrating and/or testing a PM monitor which can avoid disruption of an industrial process by using a portable apparatus which can mimic the conditions present in the industrial process and deliver a known and controllable amount of PM to a PM monitor which has been removed from a stack or duct of an industrial process and placed in a stack of the portable apparatus. By varying the PM delivered by the apparatus over a desired range of conditions, the PM monitor can be accurately tested and/or calibrated.

The present invention relates to a portable apparatus for performing calibration and/or testing of a PM emission monitor. Testing/calibration may occur in a laboratory, at the PM monitor manufacturing factory, or at an actual operating plant by removing the operating PM monitor and inserting into the apparatus. The apparatus mimics the operational behavior of the actual stack at a smaller scale. The apparatus thus comprises a stack which is scaled down in size from a much larger industrial stack, a system to generate a fluent gas stream, or upward draft, in the apparatus stack, and an associated injection system to deliver a known and controlled flow rate of PM into the scaled-down stack to entrain with the fluent gas stream through the stack.

Briefly, a PM emission monitor which is to be tested and/or calibrated is placed at a location in the scaled-down stack which is downstream of a location where PM from the injection system is introduced into the gas stream flowing through the stack. The manner of creating the fluent gas stream and the manner of introducing PM into the fluent gas stream enable the PM to be of known flow rate and be uniformly distributed within the fluent gas stream by the time the entrained PM arrives at the PM emission monitor.

In a first embodiment disclosed here, a homogeneous PM/liquid slurry is created by mixing controlled quantities of PM and liquid, such as pure water, in a mixer tank to create a specified PM/liquid ratio. Slurry is pumped from the mixer tank to a slurry inlet in a body of a nozzle which has a compressed gas inlet through which compressed gas from a compressed gas source is being introduced. The gas in the disclosed embodiments is air. The nozzle functions to atomize the slurry into a spray of small liquid droplets which are emitted from an outlet in the body of the nozzle and which contain PM.

The fluent gas stream flowing through the stack comprises a primary gas stream and a secondary gas stream. The spray is emitted from the outlet of the nozzle into the primary gas stream which is flowing axially past at least a portion of the body of the nozzle around the circumference of the nozzle body. The spray is emitted in the same general direction as the primary gas stream flow, and droplets in the spray begin to entrain with the primary gas stream after leaving the nozzle outlet. The primary gas stream flow past the nozzle body is constrained by a cylindrical axial wall which circumferentially surrounds at least a portion of the axial length of the nozzle body. The axial wall can be circular and the nozzle outlet can lie substantially on an axial centerline of the axial wall. In the disclosed embodiments, both primary and secondary gas streams utilize ambient air as their gas.

The axial wall is open at opposite ends, one of which can be considered an inlet end, and the other an outlet end. The primary gas stream enters the inlet end of the axial wall, flows through the axial wall past at least a portion of the nozzle body, and exits the outlet end of the axial wall. The nozzle outlet may be located slightly beyond the outlet end of the axial wall.

The primary gas stream is created by a primary flow fan which operates to draw ambient air into an entrance of a primary airway and force that air as primary air through the primary airway to an exit of the primary airway where primary air enters the inlet end of the axial wall for ensuing flow as a primary air stream past at least a portion of the body of the nozzle.

The open outlet end of the axial wall is disposed at an open inlet end of a stack whose size is scaled-down from that of a much larger industrial stack. The scaled-down stack has an axial stack wall which is larger in diameter than the outlet of the axial wall surrounding the nozzle. The primary air stream and the spray from the nozzle pass through the central portion of the stack wall. The larger diameter stack wall, when positioned concentrically about the outlet of the axial wall, creates an open annular space which surrounds the primary air stream and nozzle spray and into which a secondary gas stream, which uses ambient air as the gas, is introduced from an exit of a secondary airway. Ambient air is forced through the secondary airway by a secondary fan. The exit of the secondary airway is an open annular space with a specific geometric size in order to evenly distribute the secondary gas stream about the circumference of the open annular space and thereafter enter the scaled-down stack, as a secondary air stream flowing along the axial stack wall.

As it begins to flow through the stack, the secondary air stream forms an annular curtain along the stack wall, surrounding the primary air stream and the entrained spray of PM-containing droplets flowing through the central portion of the stack. The annular curtain of secondary air energizes the flow along the surface of the stack wall in order to minimize and ideally prevent impingement of PM-containing droplets onto the stack wall prior to reaching the measurement plane where the PM monitor is located.

This manner of introducing a spray of PM-containing droplets, a primary gas stream, and a secondary gas stream into the stack enables the PM to be uniformly distributed within a zone of the fluent stream by the time the entrained PM arrives at the PM emission monitor. Thus, the PM emission monitor can be tested and/or calibrated by controlling the rate at which PM is being introduced into the stack and comparing that rate to the resulting reading of the PM monitor.

This first embodiment may be considered a positive pressure embodiment because the two fans create positive pressure within the stack.

Also disclosed is a second embodiment which enables a single fan to be used. This second embodiment may be considered a negative pressure embodiment because the fan creates negative pressure within the stack.

One generic aspect of the invention relates to apparatus for testing and/or calibration of a particulate matter emission monitor which comprises a vertical cylindrical stack having an open entrance at a lower end and an open exit at an upper end.

The apparatus comprises a first wall which has a cylindrical open exit open to the open entrance of the stack. The cylindrical open exit of the first wall has a circumference inwardly spaced from a circumference of the open entrance of the stack. A second wall has a cylindrical open exit whose circumference outwardly circumscribes the circumference of the cylindrical open exit of the first wall and cooperates with the cylindrical open exit of the first wall to create between them an annular space which is open to the open entrance of the stack.

The apparatus further comprises a nozzle which has a gas inlet, a slurry inlet, and a spray outlet, and which, when slurry containing particulate matter suspended in liquid is fed into the nozzle through the slurry inlet and gas is also fed into the nozzle through the gas inlet, is operable to eject, through the spray outlet and into the stack inwardly of the open exit of the first wall, a spray of liquid droplets which contain particulate matter.

The apparatus further comprises at least one fan which is operable to create an upward draft through the cylindrical open exit of the first wall and into the stack for carrying spray droplets upwardly through the stack to a measurement/calibration plane and also to create an upward draft through the annular space between the cylindrical open exit of the first wall and the cylindrical open exit of the second wall which continues through the stack as a curtain circumscribing the upward draft which has passed through the cylindrical open exit of the first wall and is carrying the spray droplets.

Another generic aspect of the invention relates to a method for testing and/or calibration of a particulate matter emission monitor disposed at a measurement/calibration plane of a vertical stack.

The method comprises: creating an upward draft through a cylindrical open exit of a first wall and into an open entrance of the stack, and then through the stack, including through the measurement/calibration plane, to an open exit of the stack which is spaced vertically above the open entrance of the stack, and concurrently creating an upward draft through an annular space cooperatively defined by and between the cylindrical open exit of the first wall and a cylindrical open exit of a second wall, into the open entrance of the stack and continuing through the stack, as a curtain circumscribing the upward draft which has passed through the cylindrical open exit of the first wall, to the measurement/calibration plane, and from the measurement/calibration plane to the open exit of the stack.

The method further comprises creating a spray of liquid droplets which contain particulate matter, and introducing the spray into the stack for upward conveyance toward the measurement/calibration plane by the upward draft which has entered the stack through the cylindrical open exit of the first wall.

More specific aspects will be described herein with reference to the following drawings which illustrate presently preferred embodiments of the invention.

DETAILED DESCRIPTION

This disclosure incorporates by reference the content of provisional App. No. 62/330,790, filed May 2, 2016, the domestic priority benefit of which is claimed on an accompanying Application Data Sheet.

Figure 1:
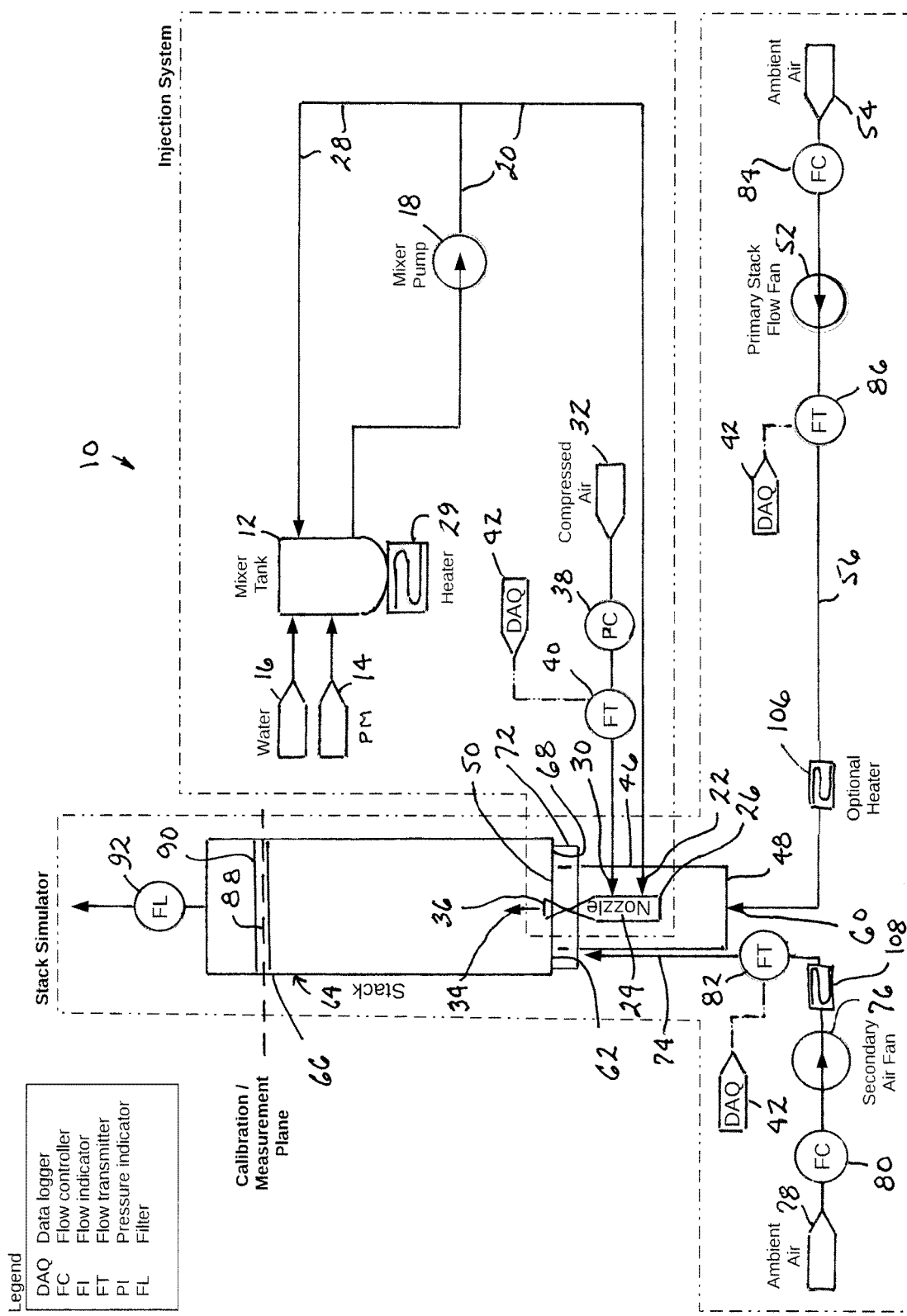
FIG. 1 is a schematic diagram of a first exemplary embodiment of the disclosed system.

FIG. 1 shows an example of apparatus 10 for testing and/or calibration of a particulate matter emission monitor which monitors particulate matter concentration in a fluent stream. Apparatus 10 comprises a mixer tank 12 in which particulate matter (PM) 14 and pure water 16 are mixed to create a homogeneous PM/liquid slurry. The quantities of PM and water introduced into mixer tank 12 are controlled to provide a specific ratio of PM to liquid.

Figure 2:
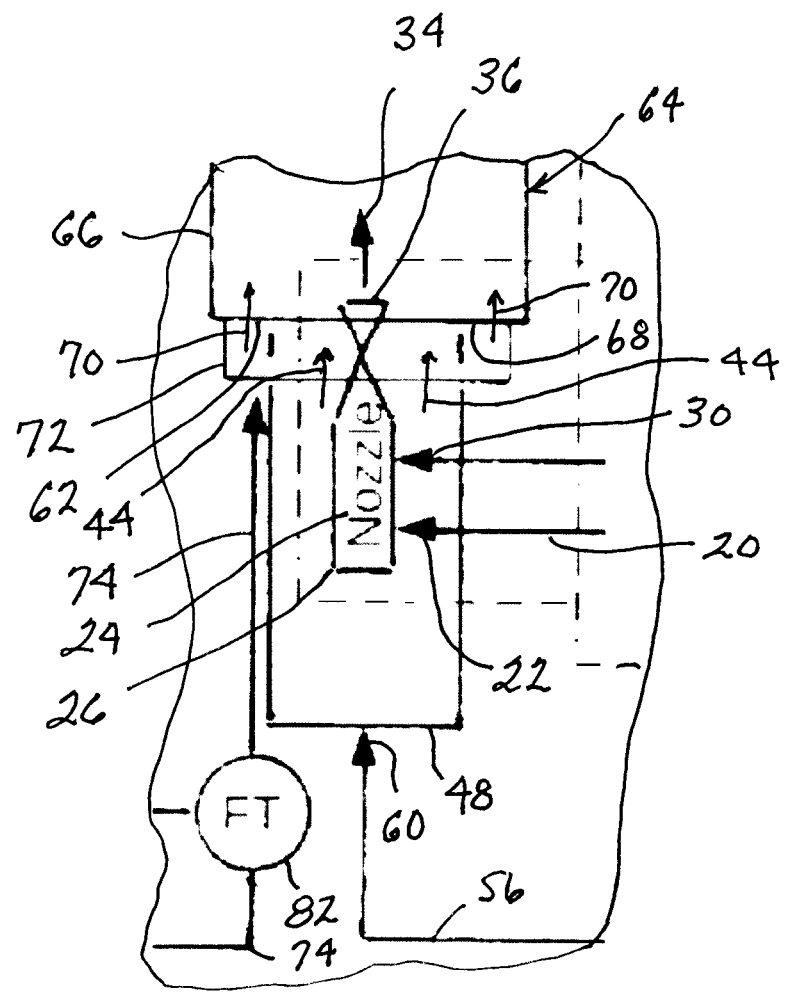
FIG. 2 is an enlargement of a portion of FIG. 1.

A mixer pump 18 operates to pump homogeneous slurry out of mixer tank 12 and through a delivery path 20 to a first inlet (slurry inlet) 22 (also marked in FIG. 2) in a body 24 of a nozzle 26, which is a dual-fluid air atomizing nozzle. The quantity of homogeneous slurry being pumped out of mixer tank 12 is a fixed rate which is in excess of the quantity of homogeneous slurry being pumped to nozzle 26. A return flow path 28 branches from delivery path 20 to return excess slurry not pumped to nozzle 26 to mixer tank 12. Slurry is returned in sufficient quantity at sufficient pressure to provide in-tank agitation for maintaining homogeneity of the slurry. A heater 29 may be optionally used to maintain a desired temperature for slurry in mixer tank 12.

Body 24 of nozzle 26 also has a second inlet (gas inlet) 30. A compressed gas source 32 provides compressed gas, such as compressed air in this instance, which is supplied to second inlet 30. Nozzle 26 functions to atomize slurry which has entered body 24 through first inlet 22 into a spray 34 of liquid droplets entrained in air which has entered through second inlet 30 and to spray atomized slurry from a spray outlet 36 in body 24. A pressure controller 38 regulates the pressure at which air from source 32 enters second inlet 30, and a flow transmitter 40 measures the flow rate at which air enters second inlet for recording by a data recorder 42. The quantity of slurry which passes through the first inlet 22 is controlled by the air pressure regulated by pressure controller 38. The remaining slurry is pumped along the return flow path 28 and re-enters the mixer tank 12.

Spray 34 is emitted into a stream of primary air 44 which is flowing axially past nozzle body 24 around the entire circumference of nozzle body 24. Spray 34 is emitted in the same general direction as the flow of primary air stream 44, and droplets in spray 34 begin to entrain with primary air stream 44 after leaving spray outlet 36. The flow of primary air stream 44 past nozzle body 24 is constrained by a cylindrical axial wall 46 which circumferentially surrounds at least a portion of the axial length of nozzle body 24. Axial wall 46 can be circular, and spray outlet 36 can lie substantially on an axial centerline of axial wall 46.

Axial wall 46 is open at opposite ends, one of which can be considered an inlet end (entrance end) 48, and the other of which, an outlet end (exit end) 50. Primary air stream 44 flows past at least a portion of nozzle body 24, and exits outlet end 50. Spray outlet 36 may be located slightly beyond outlet end 50. In this embodiment, axial wall 46 is vertical and has a uniform circumference throughout its axial length.

Primary air stream 44 is created by a primary flow fan 52 which operates to draw ambient air into an entrance 54 of a primary airway 56 and force primary air to flow through primary airway 56 to an exit 60 of primary airway 56 where primary air enters inlet end 48 of axial wall 46 for ensuing flow past nozzle 26.

Outlet end 50 of axial wall 46 is disposed at an open inlet end (open entrance) 62 of a vertical stack 64 which has a circular axial wall 66 which is larger in diameter than axial wall 46. Stack 64 is a scaled-down model of a much larger industrial stack. The circumference of axial wall 46 is inwardly spaced from that of wall 66 of stack 64 and both walls are concentric about a central vertical axis of stack 64. Primary air stream 44 creates an upward draft for carrying droplets of spray 34 upwardly through a central portion of stack 64. The larger diameter of stack wall 66 cooperates with the smaller diameter of wall 46 to create an open annular space 68 at entrance 62 of stack 64 surrounding wall 46.

A stream of secondary air 70 (FIG. 2) is introduced into stack 64 through an exit plenum 72 of a secondary airway 74 to create an upward draft circumferentially surrounding the draft which carries droplets of spray 34 upwardly through the central portion of stack 64. Exit plenum 72 comprises an axial wall whose circumference outwardly circumscribes outlet end 50 of wall 46 but is itself outwardly circumscribed by stack wall 66 in this embodiment. At an outlet end of plenum 72 an annular gap between the plenum's axial wall and stack 64 is closed by a radial wall. It is therefore through a radially inner portion of annular space 68 that secondary air 70 is introduced into stack 64. A secondary flow fan 76 operates to draw ambient air into an entrance 78 of secondary airway 74 and force secondary air through secondary airway 74, out of exit plenum 72 and into stack 64.

A flow controller 80 controls the rate at which secondary air flows through secondary airway 74, and a flow transmitter 82 measures the secondary air flow rate for recording by data recorder 42. A flow controller 84 controls the rate at which primary air flows through primary airway 56, and a flow transmitter 86 measures the primary air flow rate for recording by data recorder 42. Flow controller 80 for the secondary air stream is controlled by the primary air flow rate measured by flow transmitter 86 to maintain a specified ratio between the two flow streams that ensures a uniform flow distribution at a calibration/measurement plane 88 of a PM emission monitor 90.

As it flows through the stack, secondary air stream 70 forms an annular curtain surrounding primary air stream 44 and spray 34 flowing through the central portion of stack wall 66. The manner in which apparatus 10 creates a fluent stream through stack 64 enables the PM to be generally uniformly distributed within the fluent stream by the time the entrained PM arrives at PM emission monitor 90. A filter 92 beyond PM emission monitor 90 captures PM before the flow leaves stack 64 to enter ambient atmosphere.

Figure 3:
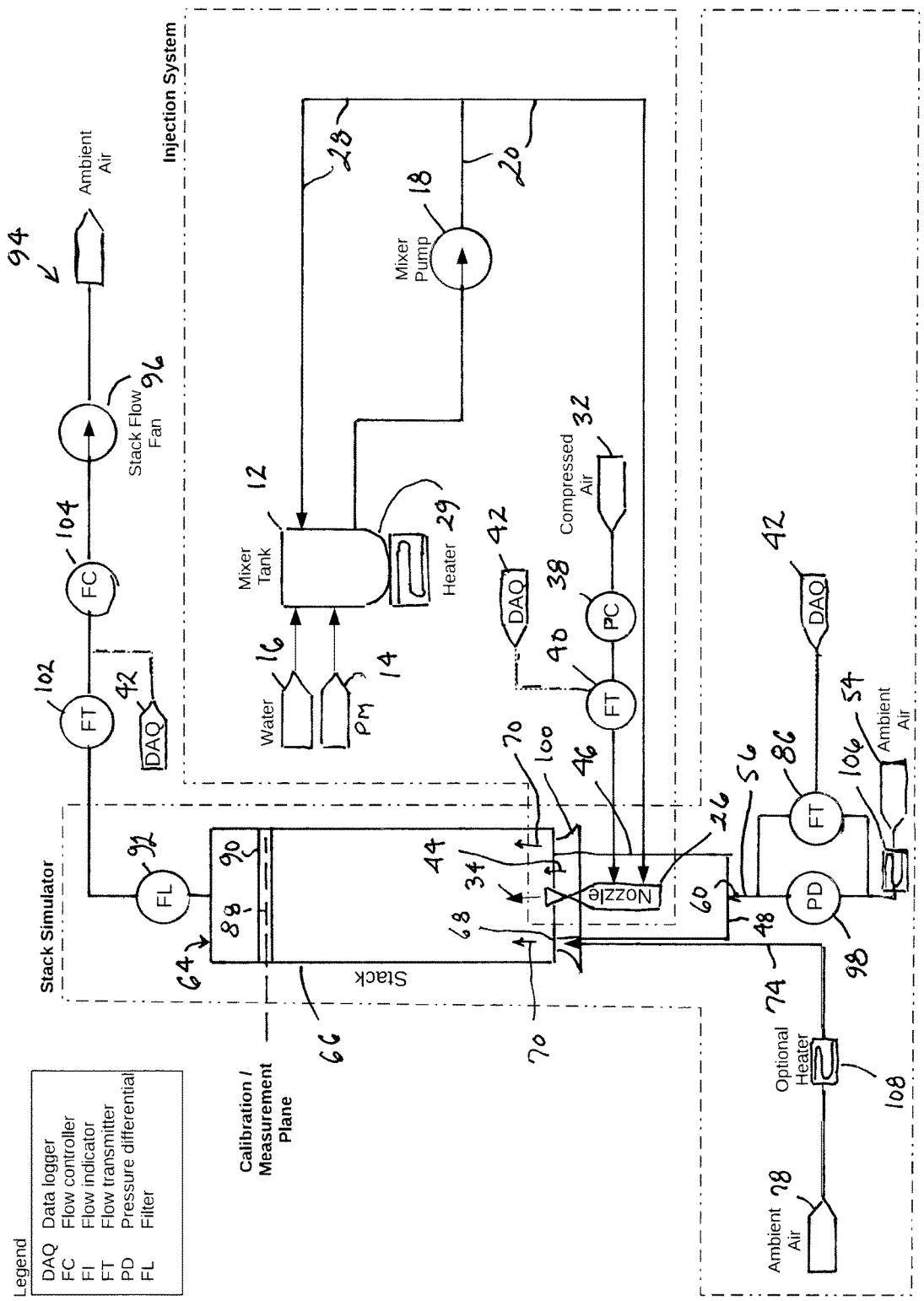
FIG. 3 is a schematic diagram of a second exemplary embodiment of the disclosed system.

FIG. 3 illustrates an embodiment 94 which is similar to embodiment 10 in FIG. 1, but differs in that a single flow fan 96 is used to draw both primary air and secondary air through the apparatus. Primary airway 56 still contains flow transmitter 86 which now measures flow by measuring pressure across a restriction 98 which creates a differential pressure between ambient air and a negative pressure created by fan 96 as the fan operates to draw primary air through inlet 48. Secondary airway 74 has no measuring or control components and therefore provides for ambient air to be drawn as secondary air through a bellmouth inlet 100 for creating uniform distribution of secondary air flow 70 into open annular space 68 around the circumference of space 68. A flow transmitter 102 and a flow controller 104 are associated with flow fan 96 to quantify the total flow within stack 64, which is the sum of flow of primary air 44 and flow of secondary air 70. Functionally, embodiment 94 differs from embodiment 10 in that whereas in embodiment 10 positive pressures force the two flows into and through stack 64, negative pressure created by fan 96 within stack 64 draws the two flows into and through stack 64.

In some industrial processes, the gas flow through a stack or duct is hot enough to evaporate all the PM-containing droplets and thus have dry PM traveling to the PM emission monitor. To assure that all PM-containing droplets sprayed into the stack will evaporate and create dry PM traveling to the PM emission monitor, optional heaters 106, 108 for heating ambient air may be used as shown in FIGS. 1 and 3.

What is claimed is:

1. Apparatus for testing and/or calibration of a particulate matter emission monitor comprising:
   a vertical cylindrical stack having an open entrance at a lower end and an open exit at an upper end;
   a first wall which has a cylindrical open exit open to the open entrance of the stack, the cylindrical open exit of the first wall having a circumference inwardly spaced from a circumference of the open entrance of the stack;
   a second wall which has a cylindrical open exit whose circumference outwardly circumscribes the circumference of the cylindrical open exit of the first wall and cooperates with the cylindrical open exit of the first wall to create between them an annular space which is open to the open entrance of the stack;
   a nozzle which has a gas inlet, a slurry inlet, and a spray outlet, and which, when slurry containing particulate matter suspended in liquid is fed into the nozzle through the slurry inlet and gas is also fed into the nozzle through the gas inlet, is operable to eject, through the spray outlet and into the stack inwardly of the open exit of the first wall, a spray of liquid droplets which contain particulate matter;
   at least one fan which is operable to create an upward draft through the cylindrical open exit of the first wall and into the stack for carrying spray droplets upwardly through the stack to a measurement/calibration plane and also to create a upward draft through the annular space between the cylindrical open exit of the first wall and the cylindrical open exit of the second wall which continues through the stack as a curtain circumscribing the upward draft which has passed through the cylindrical open exit of the first wall and is carrying the spray droplets.

2. Apparatus as set forth in claim 1 further comprising at least one heater for heating at least one of the upward drafts before entering the stack.

3. Apparatus as set forth in claim 2 in which the two heaters heat both upward drafts before entering the stack.

4. Apparatus as set forth in claim 1 further comprising a tank for holding slurry and a slurry delivery conduit for delivering slurry from the tank to the slurry inlet of the nozzle.

5. Apparatus as set forth in claim 4 further comprising a heater for heating slurry in the tank.

6. Apparatus as set forth in claim 4 further comprising a compressed gas source, a gas conduit for delivering compressed gas from the compressed gas source to the gas inlet of the nozzle, and a controller for controlling pressure of compressed gas delivered to the gas inlet of the nozzle.

7. Apparatus as set forth in claim 1 in which the first wall comprises a vertical cylinder which has a cylindrical open entrance which is vertically below the open cylindrical exit of the first wall and which is open to ambient atmosphere, and the second wall comprises a vertical cylinder which has a cylindrical open entrance which is vertically below the open cylindrical exit of the second wall and which is open to ambient atmosphere.

8. Apparatus as set forth in claim 7 in which the circumference of the open cylindrical exit of the second wall is inwardly spaced from the circumference of the open entrance of the stack.

9. Apparatus as set forth in claim 8 in which the spray outlet, the first wall, and the second wall are concentric about a central vertical axis of the stack.

10. Apparatus as set forth in claim 1 including at least one controller which controls a mass flow of at least one of the upward drafts.

11. Apparatus as set forth in claim 10 in which the upward drafts exit the stack through the open exit of the stack, and the at least one controller also controls combined mass flows of the upward drafts which exit the stack through the open exit of the stack.

12. Apparatus as set forth in claim 11 in which the at least one fan comprises a fan which is downstream of the open exit of the stack and is operable to draw the upward drafts through the stack.

13. A method for testing and/or calibration of a particulate matter emission monitor disposed at a measurement/calibration plane of a vertical stack, the method comprising:
creating an upward draft through a cylindrical open exit of a first wall, into an open entrance of the stack, and through the stack, including through the measurement/calibration plane, to an open exit of the stack which is spaced vertically above the open entrance of the stack, and concurrently creating an upward draft through an annular space cooperatively defined between the cylindrical open exit of the first wall and a cylindrical open exit of a second wall, into the open entrance of the stack and continuing through the stack, as a curtain circumscribing the upward draft which has passed through the cylindrical open exit of the first wall, to the measurement/calibration plane, and from the measurement/calibration plane to the open exit of the stack;
creating a spray of liquid droplets which contain particulate matter, and introducing the spray into the stack for upward conveyance toward the measurement/calibration plane by the upward draft which has entered the stack through the cylindrical open exit of the first wall, and using the spray of liquid droplets which contain particulate matter to perform one of testing and calibration of the particulate matter emission monitor.

14. A method as set forth in claim 13 comprising using a nozzle to create the spray by feeding particulate matter suspended in liquid into the nozzle through a slurry inlet of the nozzle and also delivering gas from a source of compressed gas into the nozzle through a gas inlet of the nozzle to cause the slurry to be atomized into the liquid droplets which contain particulate matter.

15. A method as set forth in claim 14 further comprising controlling pressure of compressed gas delivered to the gas inlet of the nozzle.

16. A method as set forth in claim 13 further comprising heating at least one of the upward drafts before entering the stack.

17. A method as set forth in claim 16 further comprising heating both upward drafts before entering the stack.

18. A method as set forth in claim 13 further comprising controlling a mass flow of at least one of the upward drafts.

19. A method as set forth in claim 18 comprising operating a fan which is downstream of the open exit of the stack to draw the upward drafts through the stack.

20. A method as set forth in claim 19 further comprising also controlling combined mass flows of the upward drafts which exit the stack through the open exit of the stack.

* * * * *